(12) United States Patent
Fadler

(10) Patent No.: US 8,494,117 B2
(45) Date of Patent: Jul. 23, 2013

(54) RADIATION THERAPY DEVICE

(75) Inventor: Franz Fadler, Hetzles (DE)

(73) Assignee: Siemens Aktiengesellschaft, München (DE)

( * ) Notice: Subject to any disclaimer, the term of this patent is extended or adjusted under 35 U.S.C. 154(b) by 283 days.

(21) Appl. No.: 12/899,189

(22) Filed: Oct. 6, 2010

(65) Prior Publication Data

US 2011/0085640 A1 Apr. 14, 2011

(30) Foreign Application Priority Data

Oct. 12, 2009 (DE) .......................... 10 2009 049 074

(51) Int. Cl.
*A61N 5/10* (2006.01)
*H05G 1/02* (2006.01)

(52) U.S. Cl.
USPC .............................. 378/65; 378/196; 378/197

(58) Field of Classification Search
USPC ...................................... 378/19, 65, 196–197
See application file for complete search history.

(56) References Cited

U.S. PATENT DOCUMENTS

| 5,095,501 | A | | 3/1992 | Kobayaski |
| 5,751,781 | A | * | 5/1998 | Brown et al. .................... 378/65 |
| 6,307,914 | B1 | * | 10/2001 | Kunieda et al. ................. 378/65 |
| 6,865,254 | B2 | * | 3/2005 | Nafstadius ...................... 378/65 |
| 6,914,959 | B2 | * | 7/2005 | Bailey et al. .................... 378/65 |
| 7,014,361 | B1 | * | 3/2006 | Ein-Gal .......................... 378/197 |
| 7,188,998 | B2 | * | 3/2007 | Gregerson et al. ............ 378/197 |
| 7,298,821 | B2 | * | 11/2007 | Ein-Gal ........................... 378/68 |
| 7,436,928 | B2 | * | 10/2008 | Urano et al. .................... 378/65 |
| 7,502,443 | B1 | | 3/2009 | Haynes et al. |
| 7,570,739 | B2 | * | 8/2009 | Bergfjord et al. ............... 378/65 |
| 7,767,988 | B2 | * | 8/2010 | Kaiser et al. ................ 250/492.3 |
| 7,796,730 | B2 | * | 9/2010 | Marash et al. ................... 378/65 |
| 7,876,881 | B2 | * | 1/2011 | Jeffery ............................ 378/65 |
| 8,223,920 | B2 | * | 7/2012 | Amelia et al. .................. 378/65 |
| 2002/0149305 | A1 | | 10/2002 | Danielsson et al. |
| 2007/0290142 | A1 | | 12/2007 | Du et al. |
| 2009/0074134 | A1 | | 3/2009 | Jeffery |

FOREIGN PATENT DOCUMENTS

| DE | 102006033501 A1 | 2/2007 |
| DE | 102007011399 A1 | 9/2008 |
| WO | WO 2008/115275 A2 | 9/2008 |

OTHER PUBLICATIONS

German Office Action dated Jun. 16, 2010 for corresponding German Patent Application No. DE 10 2009 049 074.4 with English translation.

* cited by examiner

*Primary Examiner* — Allen C. Ho
(74) *Attorney, Agent, or Firm* — Lempia Summerfield Katz LLC

(57) ABSTRACT

A radiation therapy device includes an overhanging arm, from which a therapeutic treatment beam is operable to be directed onto the object to be irradiated, the overhanging arm being attached to a rotatable holder so that the overhanging arm is operable to be rotated around an isocenter, such that the therapeutic treatment beam is operable to be directed from different angles onto the isocenter. The radiation therapy device also includes a holder ring connected to the overhanging arm, the holder ring being arranged concentrically in a plane of rotation of the radiation therapy device. The radiation therapy device includes an x-ray source for diagnostic x-rays and an x-ray detector of the diagnostic x-rays. The x-ray source and the x-ray detector are operable to be moved along the holder ring so that a diagnostic x-ray image of a patient to be irradiated is produced from different directions.

20 Claims, 4 Drawing Sheets

RADIATION THERAPY DEVICE

This application claims the benefit of DE 10 2009 049 074.4, filed Oct. 12, 2009.

BACKGROUND

The present embodiments relate to a radiation therapy device with a therapeutic radiation source, a diagnostic x-ray source and a diagnostic x-ray detector.

Radiation therapy devices with a radiation source, a diagnostic x-ray source and a diagnostic detector may be used for treating tumors. Radiation therapy devices may include an overhanging arm, from which a therapeutic treatment beam can be directed onto a patient positioned in the isocenter of the radiation therapy device.

Radiation therapy devices may include a diagnostic x-ray source and a diagnostic x-ray detector so that an image of the patient may be produced with the aid of the x-ray source and the x-ray detector. An image can, for example, be produced in advance of a planned irradiation in order to check the position of the patient and correct the position of the patient, if necessary. Such a diagnostic imaging device may also be employed during irradiation to monitor the position of the patient during the irradiation.

SUMMARY AND DESCRIPTION

The present embodiments may obviate one or more of the drawbacks or limitations in the related art. For example, in one embodiment, a radiation therapy device that images with diagnostic x-rays in a flexible manner may be specified.

The radiation therapy device of the present embodiments includes an overhanging arm, from which a therapeutic treatment beam is operable to be directed onto an object to be irradiated, the overhanging arm being attached to a rotatable holder, so that the overhanging arm is operable to be rotated around an isocenter, such that the therapeutic treatment beam is operable to be directed from different angles onto the isocenter. A holder ring is connected to the overhanging arm, such that the holder ring is essentially arranged concentrically around the isocenter in a plane of rotation of the radiation therapy device. The radiation therapy device also includes an x-ray source for diagnostic x-rays and an x-ray detector for diagnostic x-rays, the x-ray source and the x-ray detector operable to be moved along the holder ring around the isocenter so that a diagnostic x-ray image of a patient to be irradiated may be produced from different angles.

The result achieved by this arrangement is that the imaging system (e.g., the x-ray source and the x-ray detector) for diagnostic x-rays (e.g., x-rays in the kV range) may be positioned independently of the position of the overhanging arm at almost any given angle to the therapeutic treatment beam. This makes it possible to select an optimum angle between the direction of the therapeutic treatment beam and the diagnostic x-ray beam. This is especially advantageous if the movement of an organ is to be detected. Diagnostic imaging undertaken at an unfavorable position of the organs at an angle at which the organ to be observed is obscured by further structures may be avoided. The x-ray source and the x-ray detector may be moved to a desired, fixed position to generate a 2-dimensional radiographic diagnostic image from the desired position.

The overhanging arm includes beam forming elements such as, for example, a collimator that forms the beam profile before the beam from the overhanging arm strikes a patient. The patient may be positioned in the isocenter of the radiation therapy device. The rotatable holder makes it possible to rotate the overhanging arm around the isocenter so that the therapeutic treatment beam may be directed from different angles onto the patient. The holder ring is connected to the overhanging arm such that the holder ring lies in parallel to the plane of rotation of the overhanging arm.

The x-ray source and the x-ray detector are connected movably to the holder ring so that the x-ray source and the x-ray detector may be moved along and relative to the holder ring. With a fixed overhanging arm and a fixed position of the rotatable holder for the overhanging arm, the position of the x-ray source and the x-ray detector may be changed such that imaging from different directions is possible without moving the overhanging arm.

In one embodiment, the x-ray source and the x-ray detector may be moved independently of one another.

The radiation therapy device may include a control facility for controlling the position of the x-ray detector. The control facility may be configured such that, in a first operating mode, the x-ray detector is arranged in relation to the overhanging arm for recording an image of a patient that is produced by the therapeutic treatment beam and in a second operating mode, the x-ray detector is positioned opposite the x-ray source to record an image of the patient that is produced by diagnostic x-rays.

If the x-ray detector is operated in the first operating mode, the x-ray detector may detect the therapy beam passing through the patient and produce an image of the patient in the in-beam direction. This type of imaging is also referred to as MV imaging because of the energy of a therapeutic x-ray beam. In this position, the x-ray detector may be used for producing portal images, for example.

In the second operating mode, diagnostic x-ray images in the kV range may be produced. This has the advantage over imaging in the MV range that far better resolutions may be achieved in the images.

In one embodiment, the radiation therapy device includes another x-ray source for diagnostic x-rays and another x-ray detector for diagnostic x-rays. The other x-ray source and the other x-ray detector are operable to be moved along the holder ring in a similar way to the x-ray source and the x-ray detector. Fluoroscopy images may be produced from different directions with the x-ray source and the x-ray detector, and with the other x-ray source and the other x-ray detector, from which a stereoscopic image may then be created in a processor unit, for example. Compared to purely planar imaging, three-dimensional information about the structure to be monitored may be obtained.

In one embodiment, with the aid of a combination of a rotation of the rotatable holder and a movement of the x-ray source and the x-ray detector along the holder ring, an image sequence with fluoroscopy images of different orientation may be produced, from which a three-dimensional image of the patient may be reconstructed. Cone beam imaging may thus be performed. In an advantageous manner, the kV imaging system is moved by turning the rotatable holder and/or by moving the kV imaging system in relation to the holder ring. The overlaid movement enables a complete three-dimensional image data set to be created in a significantly shorter recording time and, for example, by just moving the rotatable holder. The movement of the kV imaging system in relation to the holder ring may be performed significantly more quickly than a rotation of the entire system. For example, the angles used for three-dimensional imaging may be created by a 90° rotation of the rotatable holder in combination with a movement of the kV imaging system relative to the holder ring. The movement or the combination of the different movements is controlled by the control facility.

In one embodiment, the holder ring may be moved towards the rotatable holder along the overhanging arm into a park position in the direction of the axis of rotation. The movement of the holder ring into the park position makes easier access to the patient possible.

In one embodiment, fluoroscopic images may be produced while the holder ring is being moved from the park position into the operating position. These imprecise "advance" images may be used, for example, to check whether any accessories have been attached to the patient or the patient bed, whether the position of the patient is roughly accurate, so that an advance correction may be undertaken, or to make settings on the kV imaging system for the subsequent actual imaging and to adjust the kV imaging system to the characteristics of the patient to be irradiated, which may be estimated from the "advance" images.

The rotatable holder may include a central cylindrical opening, into which the patient may be at least partly moved.

DETAILED DESCRIPTION OF THE DRAWINGS

Figure 1:
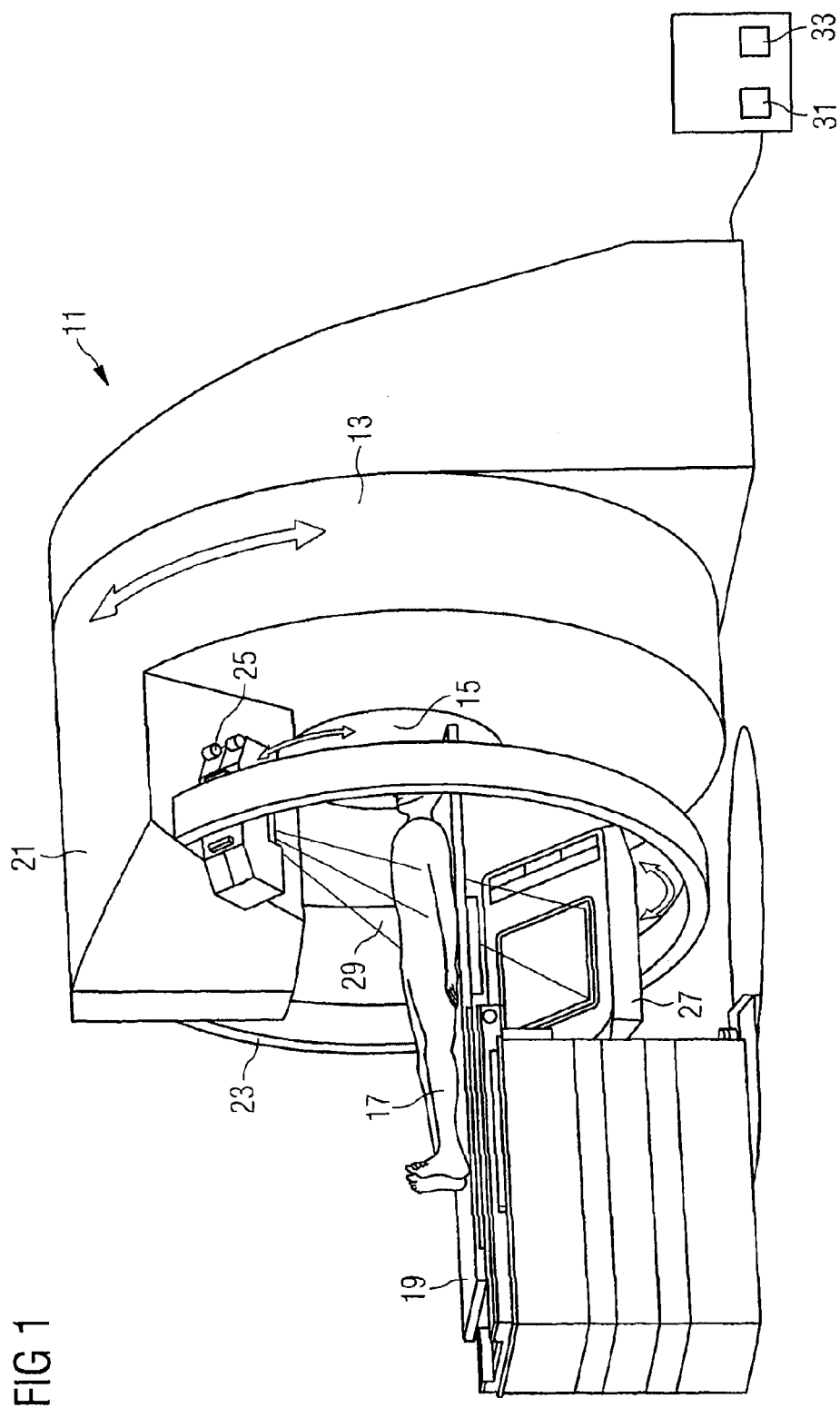
FIG. 1 shows one embodiment of a radiation therapy device with a diagnostic x-ray source and a diagnostic x-ray detector arranged on a holder ring.

FIG. 1 shows one embodiment of a radiation therapy device 11 including a rotatable gantry 13. The rotatable gantry 13 is configured in the shape of an O (e.g., ring shaped) with a cylindrical opening 15, in which the patient 17 to be irradiated may be at least partly positioned. A patient table 19 positions the patient 17, such that the tumor of the patient 17 is located in the isocenter. An overhanging arm 21 is located on the rotatable gantry 13. A beam source for a therapeutic treatment beam and a blade collimator (not shown in FIG. 1) are located at least partly in the overhanging arm 21.

A holder ring 23, which is aligned concentrically to the isocenter of the radiation therapy device and the plane of which lies in the plane of rotation of the rotatable gantry 13, is also attached to the overhanging arm 21.

A diagnostic x-ray source 25 and a diagnostic x-ray detector 27 are attached to the holder ring 23, with the x-ray source 25 and the x-ray detector 27 operable to be moved along the holder ring 23 in a controlled manner. The x-ray source 25 creates x-rays in the kV range.

FIG. 1 shows a position of the x-ray source 25 and the x-ray detector 27, in which the x-ray source and the x-ray detector 27 are lying opposite each other and are used to produce an image of the patient 17 in the kV range. A beam path of the kV x-rays 29 passes from the x-ray source 25, through the patient 17 and strikes the x-ray detector 27.

The entire gantry 13 may be rotated so that the direction of the therapy beam, from which the therapy beam strikes the patient 17, may be changed through this rotation. The holder ring 23 and thus the position of the x-ray source 25 and the position of the x-ray detector 27 are simultaneously rotated by this rotation. In addition, the x-ray detector 27 and/or the x-ray source 25 are operable to be moved independently of one another in relation to the holder ring 23, which enables the angle to be set flexibly for the diagnostic x-ray imaging.

A control facility 31 (e.g., a controller 31) controls the turning of the rotatable gantry 13 and the position of the kV imaging system (e.g., the x-ray source 25 and/or the x-ray detector 27) on the holder ring 23. An advantageous cone beam imaging may be realized with combined movement of the rotatable gantry 13 and the kV imaging system. Individual images produced from different directions are processed in a processor unit 33, and a 3D representation of the patient 17 is reconstructed.

Figure 2:
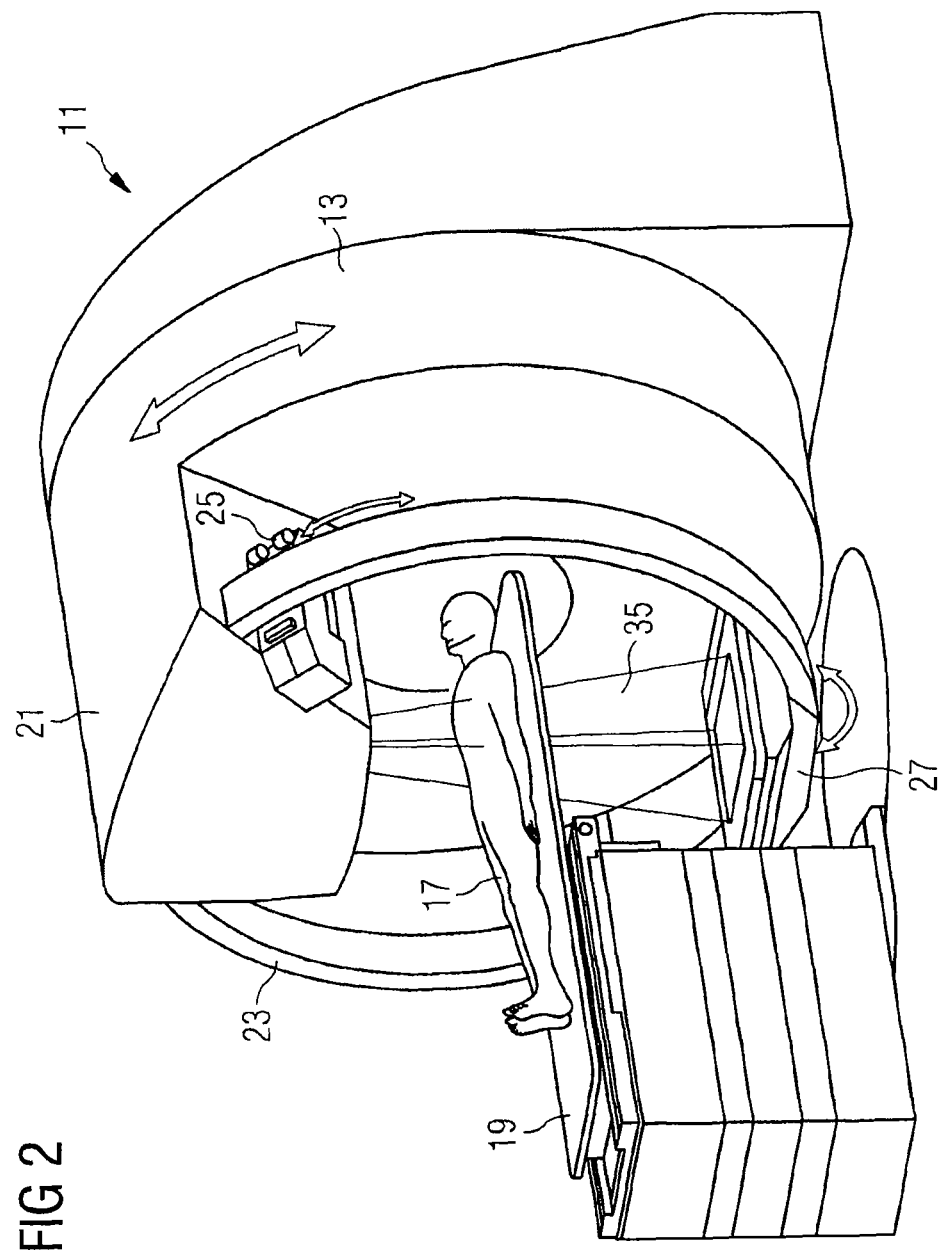
FIG. 2 shows one embodiment of the radiation therapy device of FIG. 1.

FIG. 2 shows the same radiation therapy device 11 shown in FIG. 1 or a different radiation therapy device, operated in a further operating mode. In this operating mode, the x-ray detector 27 is not arranged opposite the x-ray source 25 but is arranged opposite the overhanging arm 21. This enables the x-ray detector 27 to detect the therapy beam 35 that strikes the patient 17 from the overhanging arm 21. The patient 17 may be monitored in the therapy beam direction, and portal images may be produced.

Figure 3:
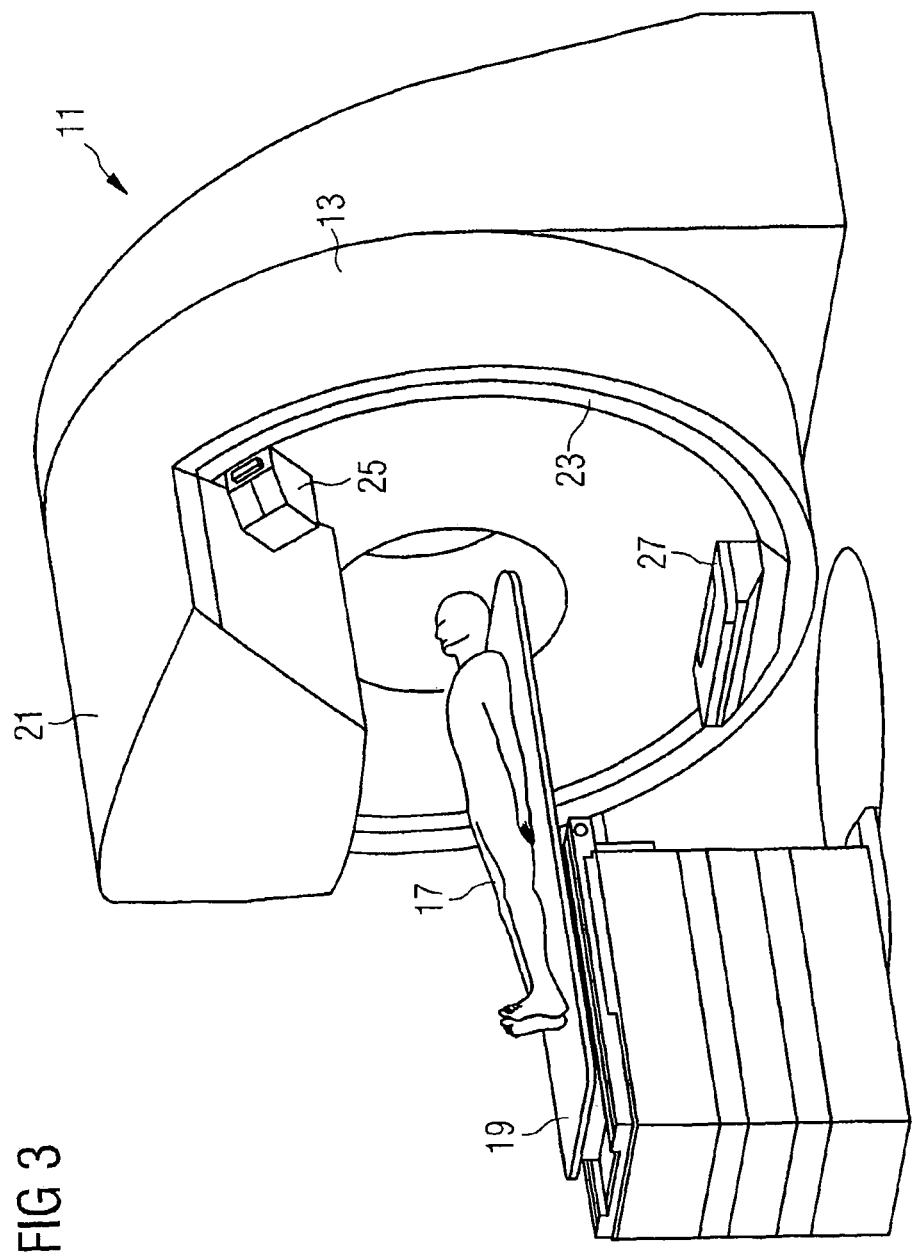
FIG. 3 shows one embodiment of the radiation therapy device of FIGS. 1 and 2 with the holder ring in the park position.

FIG. 3 shows the same radiation therapy device 11 shown in FIGS. 1 and 2 or a different radiation therapy device, with the holder ring 23 in a park position. This operation moves the holder ring 23 at least partly into a recess in the ring-shaped gantry 13. In the park position, the patient 17 may be positioned more easily for a radiation session, or a user has free access to the patient 17.

Figure 4:
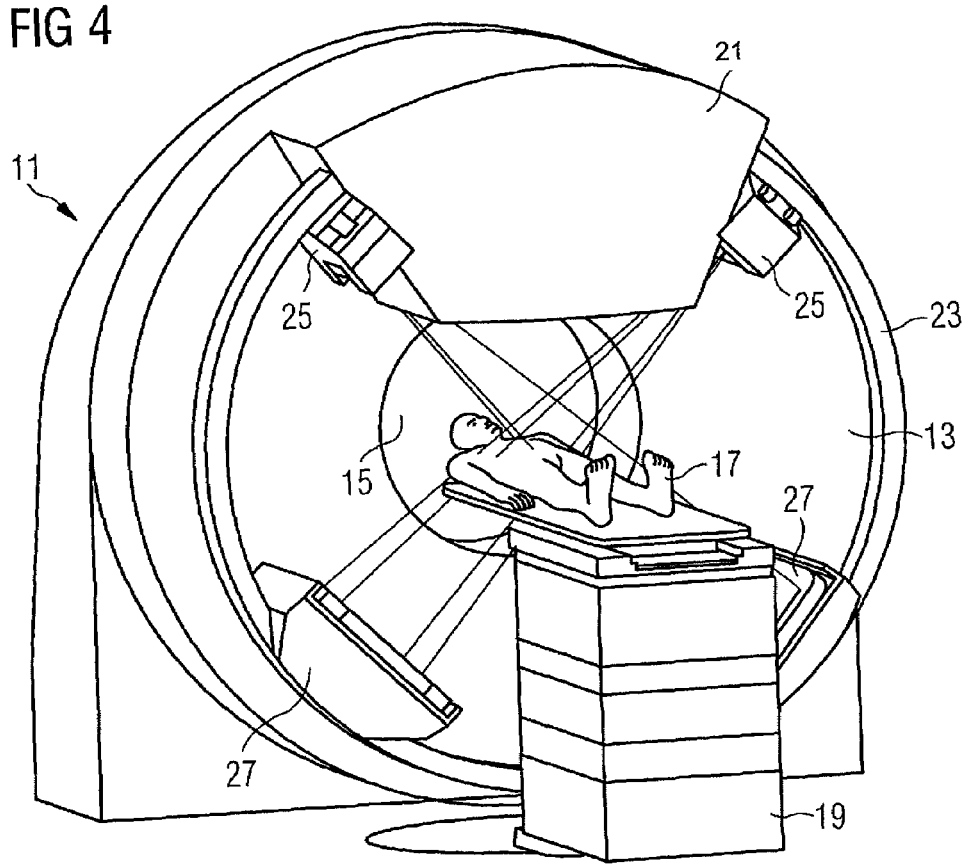
FIG. 4 shows one embodiment of a radiation therapy device with two imaging systems arranged on the holder ring.

FIG. 4 shows one embodiment of a radiation therapy device 11 that includes two diagnostic x-ray sources 25 and two diagnostic x-ray detectors 27 arranged on the holder ring 23, each being operable to move independently of the other. A position with x-ray sources 25 and x-ray detectors 27 lying opposite each other in each case is shown in FIG. 4. With the two kV imaging systems, fluoroscopic images may be produced simultaneously from different directions.

A processor unit 33 may determine a stereoscopic image of the patient 17 from the fluoroscopic images. This has the advantage that the target volume to be monitored may be monitored in three dimensions.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A radiation therapy device comprising:
   a rotatable holder;
   an overhanging arm, from which a therapeutic treatment beam is operable to be directed onto an object to be irradiated, the overhanging arm being attached to the rotatable holder so that the overhanging arm is operable to be rotated about an isocenter, such that the therapeutic treatment beam is operable to be directed from different angles onto the isocenter;
   a holder ring that is arranged concentrically in a plane of rotation of the radiation therapy device, the holder ring being connected to the overhanging arm;
   an x-ray source for emitting diagnostic x-rays; and
   an x-ray detector of the diagnostic x-rays,
   wherein the x-ray source and the x-ray detector are operable to be moved along the holder ring so that a diagnostic x-ray image of an object to be irradiated is produced from a settable direction, and wherein the x-ray source and the x-ray detector are operable to be moved independently of one another.

2. The x-ray therapy device as claimed in claim 1, further comprising a controller for controlling a position of the x-ray detector, the controller being configured such that in a first mode, the x-ray detector is arranged opposite the overhanging arm for recording an image of the object to be irradiated that is produced with the therapeutic treatment beam, and in a second mode, the x-ray detector is positioned opposite the x-ray source for recording an image of the object to be irradiated that is produced with the diagnostic x-rays.

3. The radiation therapy device as claimed in claim 2, further comprising:
another x-ray source for emitting diagnostic x-rays; and
another x-ray detector of the diagnostic x-rays,
wherein the other x-ray source and the other x-ray detector are operable to be moved along the holder ring.

4. The radiation therapy device as claimed in claim 2, wherein the combination of a rotation of the rotatable holder and a movement of the x-ray source and the x-ray detector along the holder ring is operable to produce an image chain with fluoroscopic images of different orientations, from which a three-dimensional image of the object to be irradiated is produced.

5. The radiation therapy device as claimed in claim 2, wherein the holder ring is operable to be moved towards the rotatable holder in a direction of an axis of rotation into a park position.

6. The radiation therapy device as claimed in claim 1, further comprising:
another x-ray source for emitting diagnostic x-rays; and
another x-ray detector of the diagnostic x-rays,
wherein the other x-ray source and the other x-ray detector are operable to be moved along the holder ring.

7. The radiation therapy device as claimed in claim 6, wherein the x-ray source and the x-ray detector, and the other x-ray source and the other x-ray detector, respectively, are operable to produce fluoroscopic images from different directions, from which a stereoscopic image is created.

8. The radiation therapy device as claimed in claim 7, wherein the holder ring is operable to be moved towards the rotatable holder in a direction of an axis of rotation into a park position.

9. The radiation therapy device as claimed in claim 6, wherein the combination of a rotation of the rotatable holder and a movement of the x-ray source and the x-ray detector along the holder ring is operable to produce an image chain with fluoroscopic images of different orientations, from which a three-dimensional image of the object to be irradiated is produced.

10. The radiation therapy device as claimed in claim 1, wherein the combination of a rotation of the rotatable holder and a movement of the x-ray source and the x-ray detector along the holder ring is operable to produce an image chain with fluoroscopic images of different orientations, from which a three-dimensional image of the object to be irradiated is produced.

11. The radiation therapy device as claimed in claim 10, wherein the rotatable holder comprises a central cylindrical opening, in which the object to be irradiated is at least partly positioned.

12. The radiation therapy device as claimed in claim 1, wherein the holder ring is operable to be moved towards the rotatable holder in a direction of an axis of rotation into a park position.

13. The radiation therapy device as claimed in claim 12, wherein the x-ray source and the x-ray detector are operable to be activated while the holder ring is being moved from the park position at the rotatable holder into an operating position.

14. The radiation therapy device as claimed in claim 12, wherein the rotatable holder comprises a central cylindrical opening, in which the object to be irradiated is at least partly positioned.

15. The radiation therapy device as claimed in claim 1, wherein the rotatable holder comprises a central cylindrical opening, in which the object to be irradiated is at least partly positioned.

16. A radiation therapy device comprising:
a rotatable holder;
an overhanging arm, from which a therapeutic treatment beam is operable to be directed onto an object to be irradiated, the overhanging arm being attached to the rotatable holder so that the overhanging arm is operable to be rotated about an isocenter, such that the therapeutic treatment beam is operable to be directed from different angles onto the isocenter;
a holder ring that is arranged concentrically in a plane of rotation of the radiation therapy device, the holder ring being connected to the overhanging arm;
an x-ray source for emitting diagnostic x-rays;
an x-ray detector of the diagnostic x-rays; and
a controller for controlling a position of the x-ray detector;
wherein the x-ray source and the x-ray detector are operable to be moved along the holder ring so that a diagnostic x-ray image of an object to be irradiated is produced from a settable direction, and
wherein the controller is configured such that in a first mode, the x-ray detector is arranged opposite the overhanging arm for recording an image of the object to be irradiated that is produced with the therapeutic treatment beam, and in a second mode, the x-ray detector is positioned opposite the x-ray source for recording an image of the object to be irradiated that is produced with diagnostic x-rays.

17. The radiation therapy device as claimed in claim 16, further comprising:
another x-ray source for emitting diagnostic x-rays; and
another x-ray detector of the diagnostic x-rays,
wherein the other x-ray source and the other x-ray detector are operable to be moved along the holder ring.

18. The radiation therapy device as claimed in claim 16, wherein the combination of a rotation of the rotatable holder and a movement of the x-ray source and the x-ray detector along the holder ring is operable to produce an image chain with fluoroscopic images of different orientations, from which a three-dimensional image of the object to be irradiated is produced.

19. The radiation therapy device as claimed in claim 16, wherein the holder ring is operable to be moved towards the rotatable holder in a direction of an axis of rotation into a park position.

20. A radiation therapy device comprising:
a rotatable holder;
an overhanging arm, from which a therapeutic treatment beam is operable to be directed onto an object to be irradiated, the overhanging arm being attached to the rotatable holder so that the overhanging arm is operable to be rotated about an isocenter, such that the therapeutic treatment beam is operable to be directed from different angles onto the isocenter;
a holder ring that is arranged concentrically in a plane of rotation of the radiation therapy device, the holder ring being connected to the overhanging arm;

an x-ray source for emitting diagnostic x-rays; and
an x-ray detector of the diagnostic x-rays;
wherein the x-ray source and the x-ray detector are operable to be moved along the holder ring so that a diagnostic x-ray image of an object to be irradiated is produced from a settable direction, and
wherein the rotatable holder comprises a central cylindrical opening, in which the object to be irradiated is at least partly positioned.

* * * * *